United States Patent [19]

Arena

[11] Patent Number: 4,959,467
[45] Date of Patent: Sep. 25, 1990

[54] CONTROL OF PRODUCT SELECTIVITY IN THE ADDITION OF HCN TO ARABINOSE

[75] Inventor: Blaise J. Arena, Des Plaines, Ill.

[73] Assignee: Allied-Signal Inc., Morris Township, Morris County, N.J.

[21] Appl. No.: 156,500

[22] Filed: Feb. 16, 1988

Related U.S. Application Data

[63] Continuation-in-part of Ser. No. 802,503, Nov. 27, 1985, abandoned.

[51] Int. Cl.$^5$ .......................... C07B 37/02; C07H 1/06
[52] U.S. Cl. ...................... 536/124; 536/1.1; 536/125; 536/127; 127/46.1; 558/332; 558/351
[58] Field of Search ........ 536/1.1, 55.3, 124, 536/125, 127; 127/46.1; 558/332, 334, 341, 351

[56] References Cited

U.S. PATENT DOCUMENTS

| | | | |
|---|---|---|---|
| 2,606,918 | 8/1952 | Isbell | 558/351 |
| 4,013,629 | 3/1977 | Cummisford et al. | 536/106 |
| 4,207,413 | 6/1980 | Szarek et al. | 536/1 |
| 4,262,032 | 4/1981 | Levin | 426/658 |
| 4,371,616 | 2/1983 | Huibers | 435/105 |
| 4,421,568 | 12/1983 | Huibers | 127/48 |
| 4,440,855 | 4/1984 | Horwath et al. | 435/105 |

OTHER PUBLICATIONS

J. Am. Chem. Soc. 68, 719, 793, (1946).
Ber. Deutsch, Chem. Ges, 23, 370-389, (1980).
Nature, 221, 555, (1969).
"The Theory of Sweetness", In Sweeteners & Sweetness, pp. 42-50.
"The Handbook of Sensory Physiology", vol. 4, pp. 241-245.
S. J. Angyal, Chem. Soc. Reviews, 9, 415-428, (1980).
H. J. F. Angus and Coworkers, J. Chem. Soc., 1964, 3994 and 1965, 21.
Blazer et al., J. Am. Chem. Soc. 102:5082-5085.

*Primary Examiner*—Ronald W. Griffin
*Assistant Examiner*—Nancy S. Carson
*Attorney, Agent, or Firm*—Eugene I. Snyder; Harold N. Wells; Gerard P. Rooney

[57] ABSTRACT

Hydrogen cyanide addition to a monosaccharide results in a mixture of product cyanohydrins whose ratio can be changed by conducting the hydrogen cyanide addition in the presence of an agent which forms a complex with the monosaccharide. It is preferred to add the elements of hydrogen cyanide to a preformed complex of the monosaccharide. The product selectivity appears to be dependent upon the concentration of the complexing agent up to about one molar proportion of the latter relative to the monosaccharide with the selectivity being invariant thereafter.

12 Claims, 1 Drawing Sheet

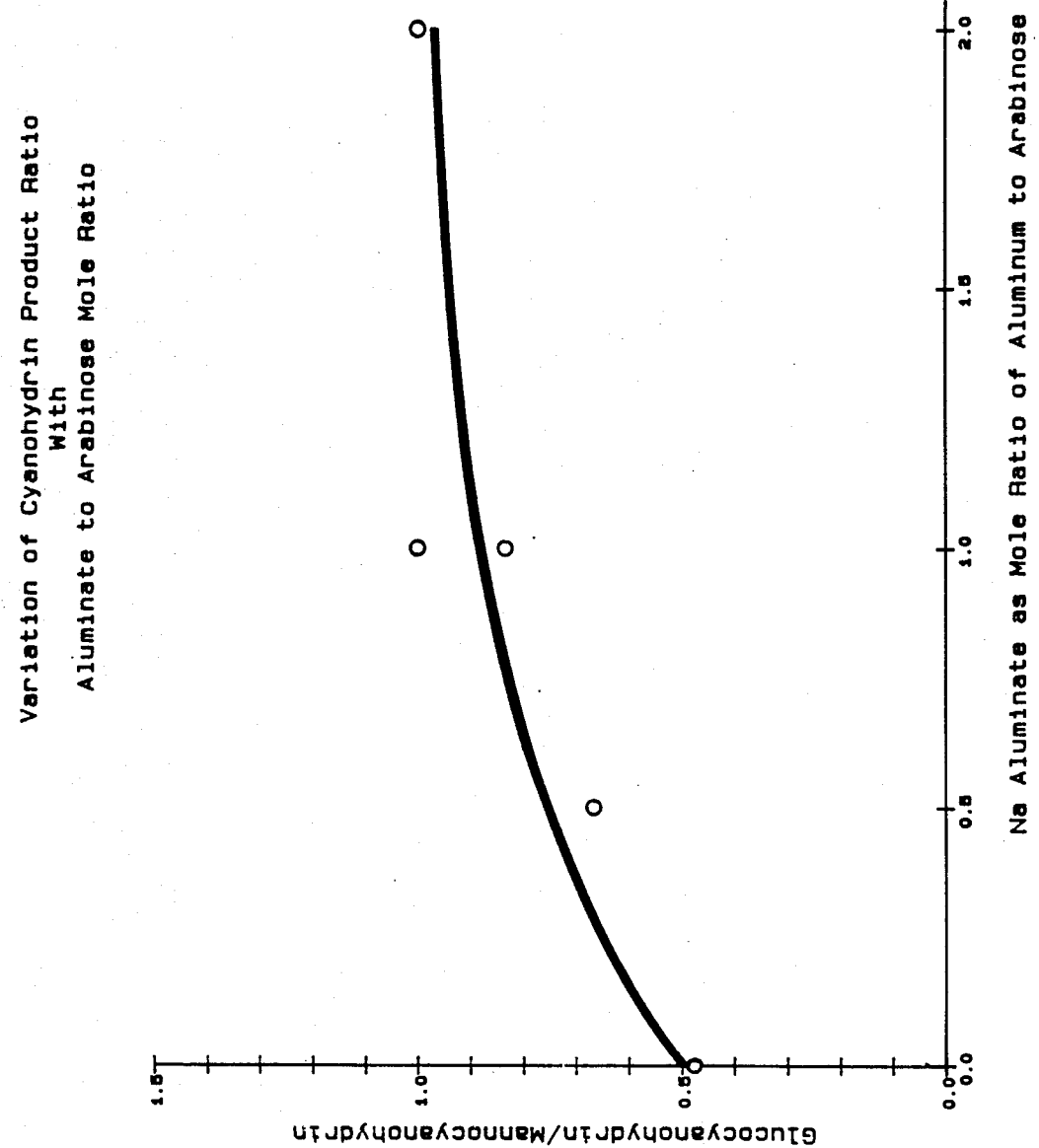

CONTROL OF PRODUCT SELECTIVITY IN THE ADDITION OF HCN TO ARABINOSE

This is a continuation-in-part of copending application(s) Ser. No. 802,503 filed on Nov. 27, 1985, now abandoned.

BACKGROUND OF THE INVENTION

Present dietetic needs, predilections, and perceptions have led to the increased use of artificial sweeteners as a replacement for the "natural" sugars, including sucrose and fructose. Such artificial sweeteners are highly imperfect, including being under continual review for their long term physiological affects, yet their demand has grown unabated. Accompanying their growth as a commercial area with substantial economic impact has been a renewed emphasis on discovering and supplying new artificial sweeteners.

The ideal artificial sweetener would be noncaloric, noncariogenic, without detrimental physiological effects, and usable by diabetics. All these requirements would be met if a sweetener were not metabolized by humans and by flora which are found in the mouth and intestinal tract, and if the sweetener were either not absorbed by humans, or absorbed without effect on any internal organ. That is, the ideal sweetener should be excreted in the same form as when ingested. Another desirable feature is that it have bulk properties similar to sucrose so that it can be substituted for table sugar in many formulations. Recently, and perhaps belatedly, attention has turned toward the L-sugars as desirable artificial sweeteners. It has been known since at least 1946 that L-fructose is sweet (M. L. Wolfrom and A. Thompson, J. Am. Chem. Soc., 68, 791,793 (1946)), and since at least 1890 that L-fructose is nonfermentable (E. Fischer, Ber. Deutsch. Chem. Ges., 23, 370,389 (1890)), hence not metabolized by microorganisms generally metabolizing D-sugars. A reasonable, although not necessarily correct, inference is that it also is not metabolized by humans. Assuming that L-fructose is a sweet nonmetabolite it becomes obvious to use it as a noncaloric sweetener in many formulations. More recently Shallenberger and coworkers have demonstrated that many L-sugars have a sweetness comparable to their D-enantiomorphs. Nature, 221, 555 (1969). Cf. R. S. Shallenberger, "The Theory of Sweetness," in Sweeteners and Sweetness, pp 42–50, Edited by G. G. Birch and coworkers; R. S. Shallenberger and T. E. Acree in "The Handbook of Sensory Physiology," Vol. 4, pp 241–5, Edited by L. M. Beider (Springer Verlag, 1971).

Exploitation of the favorable properties of L-sugars is hindered by their relative unavailability. L-Fructose, for example, is not found to any significant extent in nature. This unavailability has spurred recent efforts in developing commercially feasible methods for preparing L-sugars in amounts necessary for their use as a staple of commerce. U.S. Pat. Nos. 4,371,616 and 4,421,568 describe a method of producing L-sugars, including L-idose and L-glucose, from the readily available D-glucose. Although the preparation of a number of L-sugars is described in U.S. Pat. No. 4,262,032 the focus seems to be on typical laboratory methods wholly unsuited for economical industrial production, in contrast to the process herein. U.S. Pat. No. 4,440,855 presents a flow scheme for the preparation of a mixture of L-glucose and L-mannose. The subject matter of U.S. Pat. No. 4,207,413 is L-sucrose, the enantiomer of ordinary table sugar, which can be hydrolyzed to afford L-fructose and L-glucose.

Whatever are the details of processes, actual or proposed, for the preparation of L-sugars, many employ a cyanohydrin chain-lengthening procedure which utilizes the addition of hydrogen cyanide, or more likely the addition of the elements of hydrogen cyanide ($H^+$ and $CN^-$) via a cyanide salt under mildly basic conditions, to a lower L-monosaccharide to gain entry to the family of L-sugars. In this application the phrase "hydrogen cyanide addition" refers to synthesis of cyanohydrins by any process which results in the addition of hydrogen cyanide to the carbonyl group of a monosaccharide. Hydrogen cyanide addition affords an epimeric pair of cyanohydrins, and often only one of the pair is desired. For example, addition of HCN to L-arabinose affords a mixture of L-mannocyanohydrin and L-glucocyanohydrin, and if, say, only the latter is desired then the presence of the former is at best useless, at worst detrimental. This invention is a means of altering the cyanohydrin product ratio resulting from the addition of hydrogen cyanide to monosaccharides. Although the invention disclosed within does not achieve total selectivity in cyanohydrin formation, which would be the optimum, it does permit adjusting the ratio of cyanohydrin products over a wide range so as to increase formation of the desired product at the expense of the other cyanohydrin.

This invention is founded on my discovery that when hydrogen cyanide addition to a monosaccharide is conducted in the presence of a reagent which complexes with the monosaccharide, the ratio of resulting cyanohydrins is changed from that obtained in the absence of the complexing agent with the ratio varying with concentration of the complexing agent. This unprecedented observation then permits adjustment of the cyanohydrin product ratio over rather wide limits, which is the goal of my invention.

The formation of complex of sugars by various agents termed complexation is reasonably well known. In this application "complex" means an entity resulting from the association of a monosaccharide with a second agent. For example, a complex may result from interaction of the unshared electron pair of one or more oxygen atoms of the monosaccharide and appropriate unoccupied orbitals of a metal cation. Such an association is an equilibrium which often can be described in terms of an association or stability constant, and is established within a time period short relative to the rate of hydrogen cyanide addition to the monosaccharide. Although it appears that the majority of complexes studied to date do involve ring formation, whether such a complex is technically a chelate is not important for the purpose of this invention.

Angyal has summarized the state of knowledge of sugar-cation complexes [S. J. Angyal, Chem. Soc. Reviews,9, 415–428 (1980)] and noted that divalent and trivalent cations with an ionic radius greater than 0.8 Å complex readily with the sugar D-allose. Angyal also noted that complex formation in solution cannot be predicted from a crystal structure, citing as an example that whereas sucrose $NaBr \cdot H_2O$ is a crystallographic entity there is no noticeable complex formation between sucrose and sodium ions in solution (idem, ibid., 419). Angyal also showed that reactions may be affected by the presence of complexing cations, citing the synthesis of methyl furanosides as examples (idem, ibid., 425–7). However, there seems to be no predictability as to whether a given process will be affected by a complexing anion. Complexes between sugars and oxoanions, such as tungstate and molybdate, also have been described. H. J. F. Angus and coworkers, J. Chem. Soc., 1964, 3994; ibid. idem, 1965, 21.

There also has been a report that the proportions of epimeric cyanohydrins formed in the hydrogen cyanide addition to aldoses can be controlled with carbonate buffers of the alkali metals; U.S. Pat. No. 2,606,918. However, since neither carbonate nor alkali metals are known to complex to any significant extent with monosaccharides there is no reason to believe that the reported phenomenon results from, or is in any way connected to, complexation of the monosaccharide.

SUMMARY OF THE INVENTION

The purpose of this invention is to adjust the ratio of cyanohydrins resulting from the addition of the elements of hydrogen cyanide to a monosaccharide. An embodiment comprises conducting the hydrogen cyanide addition to monosaccharides in the presence of a reagent which complexes with the hydroxyl groups of a monosaccharide. In a more specific embodiment the reagent is sodium aluminate. In a still more specific embodiment the monosaccharide used is L-arabinose. In yet another embodiment the complexing agent is used in at least one molar proportion relative to the monosaccharides. Other embodiments and purposes will become clear from the following.

DESCRIPTION OF THE FIGURE

The FIGURE is a plot of the ratio of glucocyanohydrin to mannocyanohydrin resulting from the hydrogen cyanide addition to L-arabinose in the presence of varying concentrations of sodium aluminate.

DESCRIPTION OF THE INVENTION

Hydrogen cyanide addition to a carbonyl group appears to be a reversible reaction. Where the substrate is a monosaccharide, hydrogen cyanide addition introduces a new epimeric center, and the cyanohydrins are produced as an epimeric pair as depicted by the following equation.

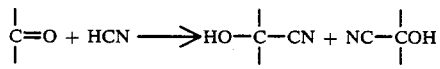

The ratio of epimeric cyanohydrins apparently is subject to thermodynamic control. I have found that if the reaction is conducted in the presence of a complexing or chelating agent the ratio of epimeric products is changed. This may be the result of the addition of the elements of hydrogen cyanide to the complexed or chelated monosaccharide instead of to the uncomplexed monosaccharide. However, this also may be the result of complexation of the epimeric cyanohydrins with an attending change in the thermodynamic property of these products, which, to the extent that the product ratio is thermodynamically controlled, results in a change in the product ratio. It is not known which of these theories, if either, is correct, but in any event the results are not dependent on any particular theory.

Any monosaccharide may be conveniently used in the practice of this invention, but the tetroses, pentoses, and hexoses generally are the most commonly used monosaccharides. Examples include threose and erythrose, which are tetroses; xylose, lyxose, ribose and arabinose as pentoses; and glucose, mannose, galactose, talose, fructose, alose, altrose, idose, and gulose as illustrative of suitable hexoses. Monosaccharides of either the L or D configuration may be equally well used, although the method which is our invention may prove most useful when the monosaccharide is an L-monosaccharide. A particularly preferred monosaccharide is L-arabinose.

The monosaccharide is then reacted with a reagent that complexes or chelates with hydroxyl groups of the monosaccharide. A general class of such reagents consists of inorganic oxoanions, as illustrated by aluminate, vanadate, chromate, molybdate, manganate, ferrate, borate, cuprate, tungstate, silicate, stannate, plumbate, and germanate anions. The particular form of the inorganic oxoanion which is used is not critical so long as it is soluble in the aqueous reaction medium. Usually the oxoanions of the alkali metals, especially sodium, potassium, and lithium, are employed for their relative availability and convenience, but it must be understood and emphasized that this is not a critical feature of my invention.

Organic derivatives of inorganic oxoanions also may be used in the practice of this invention subject to the same requirement that they be water soluble and unreactive except as a complexing agent. So, for example, such materials as aryl boronic acids, aryl phosphonic acids, aryl arsonic acids, and aryl tetrafluoroborates, pentafluorostannates, and hexafluoroantimonates can be suitably employed in the practice of this invention. Whether the inorganic oxoanions are used with a metal cation or as an organic derivative, the aluminates and borates are somewhat preferred complexing agents.

Another class of complexing agents consist of the alkaline earth and rare earth cations. These include water soluble compounds of magnesium, calcium, strontium, barium, lanthanum, cerium, praseodymium, neodymium, promethium, samarium, europium, gadolinium, terbium, dysprosium, holmium, erbium, thulium, ytterbium, and lutetium. The nature of the anion when using the cations of this class is relatively unimportant so long as the anion is unreactive and leads to a compound which is soluble in the reaction medium.

At least one molar proportion of complexing agent relative to monosaccharide is used for optimum results although the product ratio is altered even at a concentration of complexing agent as low as 0.1 molar proportion relative to monosaccharide. It is also observed that the degree of alteration varies with the concentration of complexing agent, with a maximum change in product ratio produced at a concentration of complexing agent of about 1 molar proportion relative to the monosaccharide, and at a concentration greater than that little change is observed. Hence, in the practice of my invention at least 0.1 molar proportion of complexing agent is used, and more usually 0.5–1.5 molar proportion will be employed with concentrations up to about 1 molar proportion preferred.

Generally, the method which is my invention is carried out by first preparing a mixture of complexing agent and monosaccharide, and then performing the hydrogen cyanide addition on the preformed complexed monosaccharide. Although this is the preferred practice of my invention, it is possible to add the elements of hydrogen cyanide and the complexing agent concurrently, but it needs to be recognized that when this variant is practiced the maximum change in product selectivity generally will not be obtained.

As mentioned above, the preferred practice of my invention is to add the elements of hydrogen cyanide to an aqueous solution of the monosaccharide which has been complexed with a suitable complexing agent. Hydrogen cyanide addition is effected by the reaction of a cyanide source with the complexed monosaccharide. Suitable cyanide sources include cyanide salts, such as those of alkali metals, with sodium and potassium cyanide being favored, as well as other water soluble salts furnishing cyanide iron, and hydrocyanic acid or hydrogen cyanide. Hydrogen cyanide addition generally is conducted between a pH of about 6 and about 10, but in a preferred embodiment of my invention the pH is maintained between about 7.0 and about 9.0, and most preferably between about 7.8 and about 8.2. It has been found that in the absence of this control additional products often are formed which reduce the yield of the cyanohydrins, which interfere in subsequent reactions of the process, and which may complicate the isolation of either the cyanohydrins or their subsequent reaction products. Control of pH can be conveniently effected by the addition of a weak, water soluble acid, especially carboxylic acids such as formic acid, acetic acid, propionic acid, butyric acid, valeric acid, and so on, but also by appropriate amounts of a dilute strong mineral acid, such as sulfuric acid.

Another, less conventional method of hydrogen cyanide addition is transcyanation, i.e., transfer of the elements of hydrogen cyanide from a donor cyanohydrin to a receptor monosaccharide. Complexion of the receptor monosaccharide also will be effective in controlling cyanohydrin product ratio as produced in transcyanation, and it is to be clearly understood that in the context of my invention hydrogen cyanide addition includes transcyanation.

Hydrogen cyanide addition may be conducted at any convenient temperature, with the success of the invention herein usually not dependent upon the temperature employed. Where L-arabinose is used as the monosaccharide, it has been found that the temperature at which hydrogen cyanide addition is conducted does have a significant effect on the overall reaction. Usually the temperature is maintained between about 10° and about 40° C., more desirably between about 15° and about 30° C., and most desirably between about 20° and about 25° C. It will be recognized by the skilled worker that the particular conditions of temperature may need to be determined for any set of monosaccharide and chelating agent employed.

An aqueous solution of the complexed monosaccharide may be added to the cyanide source, or the cyanide source may be added to an aqueous solution of the complexed monosaccharide. The former method is somewhat preferred but is not considered particularly critical. It has been found that a cyanide-monosaccharide ratio of 2 affords optimum results, at least with arabinose, with no advantage being offered by a relatively larger proportion of cyanide. It is somewhat desirable to conduct the addition in an inert atmosphere. By an inert atmosphere is meant a gas which does not react with any of the reactants or products of the reaction. Examples of suitable inert gases include nitrogen, helium, hydrogen, argon, krypton, xenon, neon and so forth.

This invention is illustrated below by the hydrogen cyanide addition to L-arabinose affording a mixture of L-glucocyanohydrin and L-mannocyanohydrin. It needs to be emphasized that these examples are only representative of the monosaccharide reactants which can be used and the cyanohydrin products which may be formed in hydrogen cyanide addition, and the invention is not to be limited thereto.

EXAMPLE 1

Complexation as evidenced by NMR data. Aqueous solutions of L-arabinose containing 1 molar proportion of complexing agent were prepared. The $C^{13}$-NMR spectrum was recorded and the chemical shift measured at carbon number one for both the alpha and beta anomers, respectively. The chemical shift of carbon number one of the complexed $\alpha$ and $\beta$ anomers of L-arabinose was then subtracted from the chemical shift of the corresponding uncomplexed anomer to give a net change in chemical shift brought about by complexation, $\delta C_1(\alpha)$ and $\delta C_1(\beta)$, respectively. These changes are summarized in the following table, which also shows that the chemical shifts for two mixtures were so pronounced that their identification was not possible.

TABLE 1

| $C^{13}$ Chemical Shifts for Complexed L-Arabinose Relative to Uncomplexed L-Arabinose | | |
|---|---|---|
| Complexing Agent | $C_1(\alpha)$ | $C_1(\beta)$ |
| $Ca^{+2}$ | −1.1 | −1.1 |
| $La^{+3}$ | −0.9 | −1.0 |
| $WO_4^=$ | −0.5 | −0.4 |
| $MoO_4^=$ | +0.1 | +0.1 |
| $Al(OH)_4^-$ | +4.8 | +5.5 |
| $B_4O_7^=$ | not identified | |
| $C_6H_5BO_2^=$ | not identified | |

These data demonstrate the interaction between various complexing agents and L-arabinose as representative of monosaccharides, and provide experimental support for complexation which importantly influences $C_1$, the site of hydrogen cyanide addition.

EXAMPLE 2

Effect of sodium aluminate concentration on cyanohydrin product ratio. To a solution of 15.0 g of sodium cyanide in 100 ml of deionized water was added concentrated acetic acid, with cooling under nitrogen, to pH 8.0. Separately, a solution containing 25.0 g of L-arabinose in 100 ml of deionized water containing variable amounts of sodium aluminate was prepared. The latter solution then was added slowly to the agitated solution of sodium cyanide with the pH being continuously maintained at 8.0+0.2 by the addition of acetic acid. The mixture was stirred for 1 hour, at which time the reaction appeared to be essentially complete, and the pH was adjusted to 2.0 by the addition of concentrated sulfuric acid with cooling. The product mixture was analyzed by $C^{13}$-NMR with the results tabulated below, where the molar ratio of aluminate:L-arabinose is the mole ratio of aluminum in aluminate to arabinose.

TABLE 2

| Cyanohydrin Ratio as a Function of Molar Ratio of Aluminate | |
|---|---|
| Ratio of Cyanohydrins of Mannose:Glucose | Molar Ratio of Aluminate:L-Arabinose |
| 2.1 | 0 |
| 1.5 | 0.5:1 |
| 1.1 | 1:1 |

TABLE 2-continued

Cyanohydrin Ratio as a Function of Molar Ratio of Aluminate

| Ratio of Cyanohydrins of Mannose:Glucose | Molar Ratio of Aluminate:L-Arabinose |
|---|---|
| 1.0 | 2:1 |

These results are also displayed in the FIGURE, which clearly shows the dependence of the mannocyanohydrin:glucocyanohydrin ratio as a function of sodium aluminate concentration, at least up to about a 1 molar proportion of the latter.

EXAMPLE 3

Effect of different chelating agents on product ratio. Hydrogen cyanide addition to L-arabinose chelated with one molar proportion of various chelating agents was performed essentially as described above. The product mixture was analyzed by $C^{13}$-NMR and the results are tabulated below.

TABLE 3

Cyanohydrin Ratio as a Function of Various Chelating Agents

| Chelating Agent | Ratio of Cyanohydrins of Mannose:Glucose | Ratio of Cyanohydrins of Glucose:Mannose |
|---|---|---|
| none (control) | 2:1 | 0.5:1 |
| La(III) acetate1. | 1.4:1 | 0.7:1 |
| sodium aluminate | 1:1 | 1:1 |
| sodium borate | 1:1 | 1:1 |
| phenyl boronic acid | 0.7:1 | 1.4:1 |

Although in the absence of any chelating agent the ratio of cyanohydrins of glucose:mannose is 0.5:1, this can be changed to a ratio as high as 1.4:1 using phenyl boronic acid. This example is intended to illustrate the versatility of this method without in any way implying that this is the limiting upper ratio which can be obtained.

What is claimed is:

1. In the method of making a mixture of L-glucose cyanohydrin and L-mannose cyanohydrin by hydrogen cyanide addition to an aqueous solution of L-arabinose, the improvement comprising increasing the relative amount of L-glucose cyanohydrin in the cyanohydrin mixture by effecting the hydrogen cyanide addition to L-arabinose in the presence of at least 0.1 molar proportions of a reagent selected from the group consisting of water soluble aluminates, vanadates, chromates, molybdates, manganates, ferrates, borates, cuprates, tungstates, silicates, stannates, plumbates, germanates, and rare earth salts.

2. The method of claim 1 where the complexing agent is an inorganic aluminate or borate.

3. The method of claim 1 where the complexing agent is an organic aluminate or borate.

4. The method of claim 1 where the complexing agent is used in an amount up to about one molar proportion relative to L-arabinose.

5. A method of controlling the cyanohydrin product ratio in hydrogen cyanide addition to monosaccharides comprising reacting the elements of hydrogen cyanide with an aqueous solution of a complex of the monosaccharide resulting from complexation of the monosaccharide with an agent which complexes hydroxyl groups of monosaccharides, said complexing agent being selected from the group consisting of water soluble aluminates, vanadates, chromates, molybdates, manganates, ferrates, borates, cuprates, tungstate, silicates, stannates, plumbates, germanates or rare earth salts.

6. The method of claim 5 where the monosaccharide is selected from the group consisting of tetroses, pentoses, and hexoses.

7. The method of claim 6 where the monosaccharide is a tetrose or pentose selected from the group consisting of erythrose, threose, arabinose, ribose, lyxose, and xylose.

8. The method of claim 7 where the monosaccharide is L-arabinose.

9. The method of claim 6 where the monosaccharide is a hexose.

10. The method of claim 5 where the complexing agent is an inorganic aluminate or borate.

11. The method of claim 5 where the complexing agent is an organic aluminate or borate.

12. The method of claim 5 where the complexing agent is used in an amount up to about one molar proportion relative to the monosaccharide.

* * * * *